United States Patent
Litvak et al.

(10) Patent No.: US 9,597,502 B2
(45) Date of Patent: Mar. 21, 2017

(54) SYSTEMS AND METHODS FOR CONTROLLING A WIDTH OF AN EXCITATION FIELD CREATED BY CURRENT APPLIED BY A COCHLEAR IMPLANT SYSTEM

(71) Applicant: ADVANCED BIONICS AG, Staefa (CH)

(72) Inventors: Leonid M. Litvak, Los Angeles, CA (US); Michael S. Marzalek, Santa Rosa, CA (US)

(73) Assignee: Advanced Bionics AG, Staefa (CH)

( * ) Notice: Subject to any disclaimer, the term of this patent is extended or adjusted under 35 U.S.C. 154(b) by 34 days.

(21) Appl. No.: 14/651,628

(22) PCT Filed: Nov. 29, 2013

(86) PCT No.: PCT/US2013/072492
§ 371 (c)(1),
(2) Date: Jun. 11, 2015

(87) PCT Pub. No.: WO2014/093036
PCT Pub. Date: Jun. 19, 2014

(65) Prior Publication Data
US 2015/0328457 A1 Nov. 19, 2015

Related U.S. Application Data

(60) Provisional application No. 61/737,676, filed on Dec. 14, 2012.

(51) Int. Cl.
*A61N 1/00* (2006.01)
*A61N 1/36* (2006.01)
*A61N 1/05* (2006.01)

(52) U.S. Cl.
CPC ....... *A61N 1/36032* (2013.01); *A61N 1/0541* (2013.01); *F04C 2270/0421* (2013.01)

(58) Field of Classification Search
USPC .............................................. 606/21, 23, 48
See application file for complete search history.

(56) References Cited

U.S. PATENT DOCUMENTS 7,110,821 B1 9/2006 Ross
7,769,467 B1 8/2010 Emadi et al.
(Continued)

OTHER PUBLICATIONS

Partial International Search Report received in International Application No. PCT/US13/072492, dated Apr. 22, 2014.
(Continued)

*Primary Examiner* — Nicole F Johnson
(74) *Attorney, Agent, or Firm* — ALG Intellectual Property, LLC

(57) ABSTRACT

An exemplary sound processor (104) 1) identifies a stimulation site within a cochlea of a patient that is to be stimulated in order to represent acoustic content presented to the patient, the stimulation site included within a plurality of stimulation sites associated with a stimulation channel corresponding to a plurality of electrodes, 2) determines a target excitation field width associated with the stimulation channel and 3) dynamically sets, based on the identified stimulation site, an amplitude and a polarity of current to be applied to each electrode included in the plurality of electrodes in order to represent the acoustic content so that an excitation field created by the current has a width that roughly matches the target excitation field width. A system and a corresponding method are also disclosed.

20 Claims, 10 Drawing Sheets

(56) References Cited

U.S. PATENT DOCUMENTS

| | | |
|---|---|---|
| 7,860,573 B2 | 12/2010 | van den Honert |
| 7,899,547 B1 | 3/2011 | Emadi |
| 2009/0264960 A1 | 10/2009 | Litvak et al. |
| 2010/0106218 A1* | 4/2010 | Botros ................ A61B 5/0031 |
| | | 607/57 |
| 2011/0077710 A1 | 3/2011 | Saoji et al. |
| 2011/0077712 A1* | 3/2011 | Killian .................... A61B 5/12 |
| | | 607/57 |
| 2012/0179223 A1 | 7/2012 | Saoji et al. |

OTHER PUBLICATIONS

International Search Report and Written Opinion received in International Application No. PCT/US13/072492, dated Aug. 29, 2014.

\* cited by examiner

SYSTEMS AND METHODS FOR CONTROLLING A WIDTH OF AN EXCITATION FIELD CREATED BY CURRENT APPLIED BY A COCHLEAR IMPLANT SYSTEM

RELATED APPLICATIONS

The present application claims priority to U.S. Provisional Patent Application No. 61/737,676, filed Dec. 14, 2012, the contents of which are hereby incorporated by reference in their entirety.

BACKGROUND INFORMATION

Current steering is often used in cochlear implant systems to more effectively represent sound presented to cochlear implant patients. In traditional current steering strategies, weighted stimulation current is applied concurrently to two adjacent electrodes by a cochlear implant system in order to stimulate a stimulation site located in between areas associated with the electrodes. In this manner, the cochlear implant system may create a perception of a frequency in between the frequencies associated with the electrodes.

While current steering is effective in augmenting sound perception, it may introduce spectral broadening. In other words, an excitation field created by the current steering may be relatively wider than that created by stimulation of a single electrode (which may occur when the frequency of interest corresponds directly with the electrode). The spectral broadening may result in the patient perceiving a relatively noisier tone than what the patient may perceive when the single electrode is stimulated. Such fluctuations in noise perception may be undesirable and frustrating for the patient.

BRIEF DESCRIPTION OF THE DRAWINGS

The accompanying drawings illustrate various embodiments and are a part of the specification. The illustrated embodiments are merely examples and do not limit the scope of the disclosure. Throughout the drawings, identical or similar reference numbers designate identical or similar elements.

DETAILED DESCRIPTION

Systems and methods for controlling a width of an excitation field created by current applied by a cochlear implant system are described herein. As will be described below, a sound processor included in a cochlear implant system may 1) identify a stimulation site within a cochlea of a patient that is to be stimulated in order to represent acoustic content presented to the patient, the stimulation site included within a plurality of stimulation sites associated with a stimulation channel corresponding to a plurality of electrodes, 2) determine a target excitation field width associated with the stimulation channel, and 3) dynamically set, based on the identified stimulation site, an amplitude and a polarity of current to be applied to each electrode included in the plurality of electrodes in order to represent the acoustic content so that an excitation field created by the current has a width that roughly matches the target excitation field width.

As used herein, an "excitation field width" may refer to a physical width (e.g., a physical distance within the cochlea), a neural space width (e.g., constancy in the neural space), and/or a perceptual width (e.g., a quality of tone as perceived by the patient). An excitation field width that "roughly matches" a target excitation field width refers to an excitation field width that is within a predetermined amount (e.g., distance) of the target excitation field width. For example, a first excitation field that has a width that roughly matches a width of a second excitation field may be perceived by the patient as having roughly the same quality or noise level.

By dynamically setting the amplitude and polarity of current to be applied to each electrode in order to represent the acoustic content, the systems and methods described herein may facilitate a relatively constant excitation field width for a particular stimulation channel, regardless of the location of the desired stimulation site within the stimulation channel. This may improve patient perception of the audio content, minimize fluctuations in perceived noise levels within the stimulation channel, and reduce power consumption by the cochlear implant system.

Figure 1:
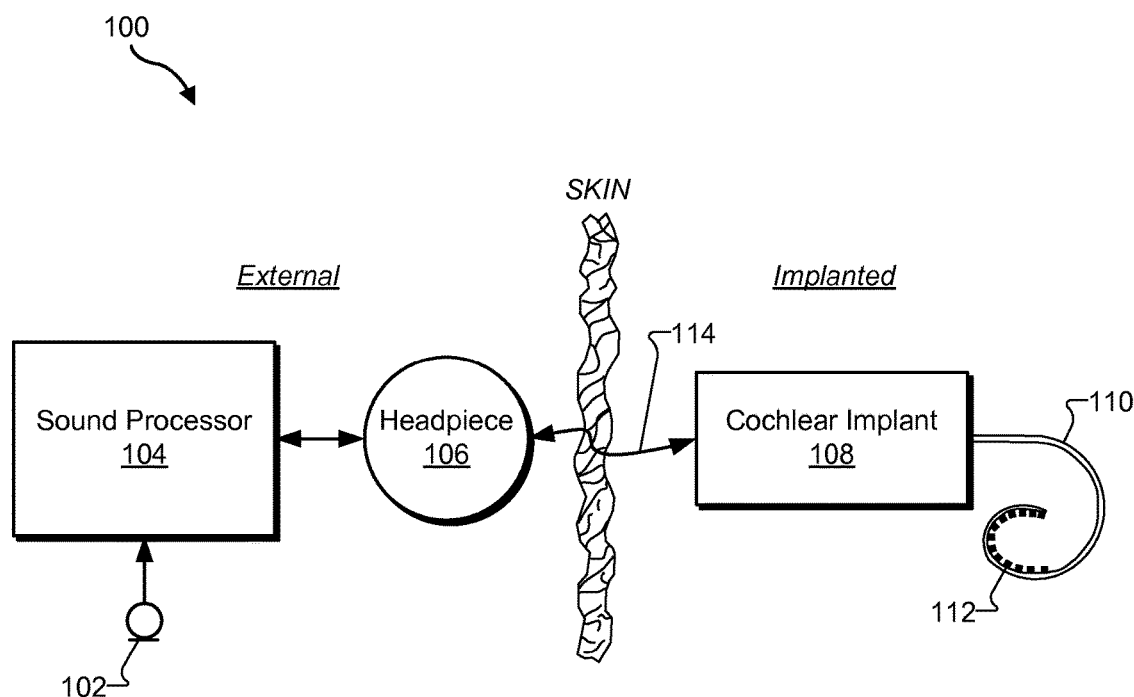
FIG. 1 illustrates an exemplary cochlear implant system according to principles described herein.

FIG. 1 illustrates an exemplary cochlear implant system 100. As shown, cochlear implant system 100 may include various components configured to be located external to a patient including, but not limited to, a microphone 102, a sound processor 104, and a headpiece 106. Cochlear implant system 100 may further include various components configured to be implanted within the patient including, but not limited to, a cochlear implant 108 and a lead 110 (also referred to as an electrode array) with a plurality of electrodes 112 disposed thereon. As will be described in more detail below, additional or alternative components may be included within cochlear implant system 100 as may serve a particular implementation. The components shown in FIG. 1 will now be described in more detail.

Microphone 102 may be configured to detect audio signals presented to the patient. Microphone 102 may be implemented in any suitable manner. For example, microphone 102 may include a microphone that is configured to be placed within the concha of the ear near the entrance to the ear canal, such as a T-MIC™ microphone from Advanced Bionics. Such a microphone may be held within the concha of the ear near the entrance of the ear canal by a boom or stalk that is attached to an ear hook configured to be selectively attached to sound processor 104. Additionally or alternatively, microphone 102 may be implemented by one or more microphones disposed within headpiece 106, one or more microphones disposed within sound processor 104, one or more beam-forming microphones, and/or any other suitable microphone as may serve a particular implementation.

Sound processor 104 (i.e., one or more components included within sound processor 104) may be configured to direct cochlear implant 108 to generate and apply electrical stimulation (also referred to herein as "stimulation current") representative of one or more audio signals (e.g., one or more audio signals detected by microphone 102, input by way of an auxiliary audio input port, etc.) to one or more stimulation sites associated with an auditory pathway (e.g., the auditory nerve) of the patient. Exemplary stimulation sites include, but are not limited to, one or more locations within the cochlea, the cochlear nucleus, the inferior colliculus, and/or any other nuclei in the auditory pathway. To this end, sound processor 104 may process the one or more audio signals in accordance with a selected sound processing strategy or program to generate appropriate stimulation parameters for controlling cochlear implant 108. Sound processor 104 may include or be implemented by a behind-the-ear ("BTE") unit, a body worn device, and/or any other sound processing unit as may serve a particular implementation. For example, sound processor 104 may be implemented by an electro-acoustic stimulation ("EAS") sound processor included in an EAS system configured to provide electrical and acoustic stimulation to a patient.

In some examples, sound processor 104 may wirelessly transmit stimulation parameters (e.g., in the form of data words included in a forward telemetry sequence) and/or power signals to cochlear implant 108 by way of a wireless communication link 114 between headpiece 106 and cochlear implant 108. It will be understood that communication link 114 may include a bi-directional communication link and/or one or more dedicated uni-directional communication links.

Headpiece 106 may be communicatively coupled to sound processor 104 and may include an external antenna (e.g., a coil and/or one or more wireless communication components) configured to facilitate selective wireless coupling of sound processor 104 to cochlear implant 108. Headpiece 106 may additionally or alternatively be used to selectively and wirelessly couple any other external device to cochlear implant 108. To this end, headpiece 106 may be configured to be affixed to the patient's head and positioned such that the external antenna housed within headpiece 106 is communicatively coupled to a corresponding implantable antenna (which may also be implemented by a coil and/or one or more wireless communication components) included within or otherwise associated with cochlear implant 108. In this manner, stimulation parameters and/or power signals may be wirelessly transmitted between sound processor 104 and cochlear implant 108 via a communication link 114 (which may include a bi-directional communication link and/or one or more dedicated uni-directional communication links as may serve a particular implementation).

Cochlear implant 108 may include any type of implantable stimulator that may be used in association with the systems and methods described herein. For example, cochlear implant 108 may be implemented by an implantable cochlear stimulator. In some alternative implementations, cochlear implant 108 may include a brainstem implant and/or any other type of active implant or auditory prosthesis that may be implanted within a patient and configured to apply stimulation to one or more stimulation sites located along an auditory pathway of a patient.

In some examples, cochlear implant 108 may be configured to generate electrical stimulation representative of an audio signal processed by sound processor 104 (e.g., an audio signal detected by microphone 102) in accordance with one or more stimulation parameters transmitted thereto by sound processor 104. Cochlear implant 108 may be further configured to apply the electrical stimulation to one or more stimulation sites within the patient via one or more electrodes 112 disposed along lead 110 (e.g., by way of one or more stimulation channels formed by electrodes 112). In some examples, cochlear implant 108 may include a plurality of independent current sources each associated with a channel defined by one or more of electrodes 112. In this manner, different stimulation current levels may be applied to multiple stimulation sites simultaneously (also referred to as "concurrently") by way of multiple electrodes 112.

Figure 2:
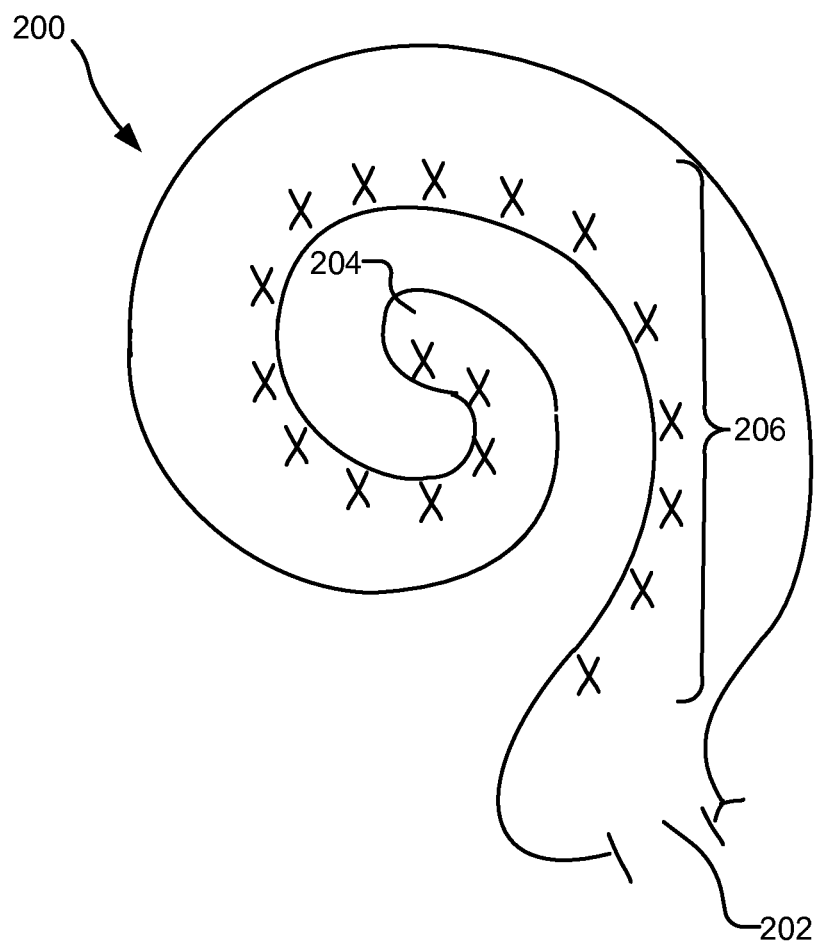
FIG. 2 illustrates a schematic structure of the human cochlea according to principles described herein.

FIG. 2 illustrates a schematic structure of the human cochlea 200 into which lead 110 may be inserted. As shown in FIG. 2, the cochlea 200 is in the shape of a spiral beginning at a base 202 and ending at an apex 204. Within the cochlea 200 resides auditory nerve tissue 206, which is denoted by Xs in FIG. 2. The auditory nerve tissue 206 is organized within the cochlea 200 in a tonotopic manner. Relatively low frequencies are encoded at or near the apex 204 of the cochlea 200 (referred to as an "apical region") while relatively high frequencies are encoded at or near the base 202 (referred to as a "basal region"). Hence, each location along the length of the cochlea 200 corresponds to a different perceived frequency. Cochlear implant system 100 may therefore be configured to apply electrical stimulation to different locations within the cochlea 200 (e.g., different locations along the auditory nerve tissue 206) to provide a sensation of hearing.

Figure 3:
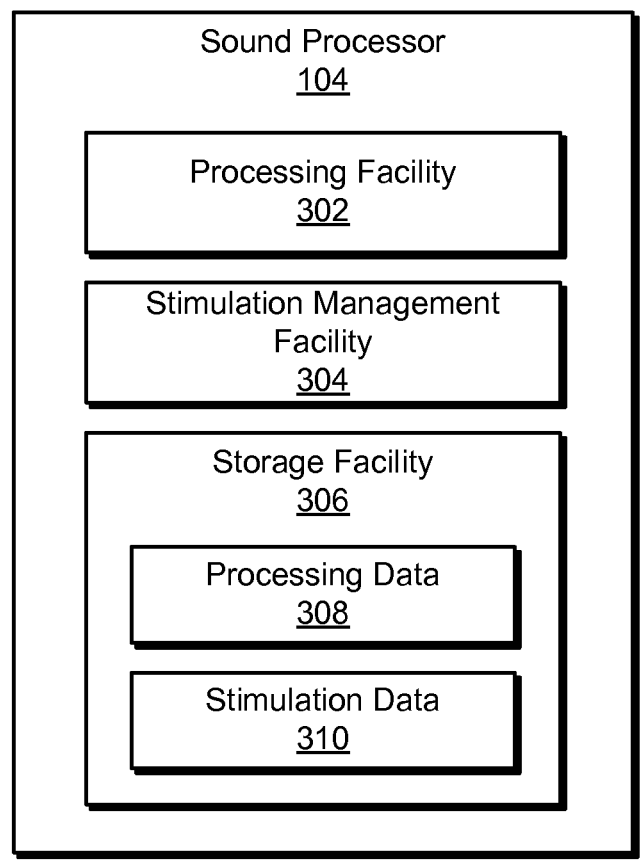
FIG. 3 illustrates exemplary components of a sound processor according to principles described herein.

FIG. 3 illustrates exemplary components of sound processor 104. It will be recognized that the components shown in FIG. 3 are merely representative of the many different components that may be included in sound processor 104 and that sound processor 104 may include additional or alternative components as may serve a particular implementation.

As shown in FIG. 3, sound processor 104 may include a processing facility 302, a stimulation management facility 304, and a storage facility 306, which may be in communication with one another using any suitable communication technologies. Storage facility 306 may be configured to maintain processing data 308 generated and/or used by processing facility 302, and stimulation data 310 (e.g., data representative of one or more stimulation parameters) generated and/or used by stimulation management facility 304. Storage facility 306 may maintain additional or alternative data as may serve a particular implementation. One or more of facilities 302-306 may include a computing device or processor configured to perform one or more of the functions described herein. Facilities 302-306 will now be described in more detail.

Processing facility 302 may be configured to process an audio signal presented to a cochlear implant patient (e.g., an audio signal detected by microphone 102, an audio signal input by way of an auxiliary audio input port, etc.). For example, processing facility 302 may perform one or more pre-processing operations, spectral analysis operations, noise reduction operations, mapping operations, and/or any other types of signal processing operations on a detected audio signal as may serve a particular application.

In some examples, processing facility 302 may divide an audio signal presented to a cochlear implant patient into a plurality of analysis channels each containing a frequency domain signal (also referred to herein as "acoustic content") representative of a distinct frequency portion of the audio signal. This may be performed in any suitable manner. For example, processing facility 302 may be implemented by a plurality of band-pass filters configured to divide the audio signal into a plurality of frequency channels or bands. Additionally or alternatively, processing facility 302 may be configured to convert the audio signal from a time domain into a frequency domain and then divide the resulting frequency bins into the plurality of analysis channels. To this end, processing facility 302 may include one or more components configured to apply a Discrete Fourier Transform (e.g., a Fast Fourier Transform ("FFT")) to the audio signal.

Figure 4:
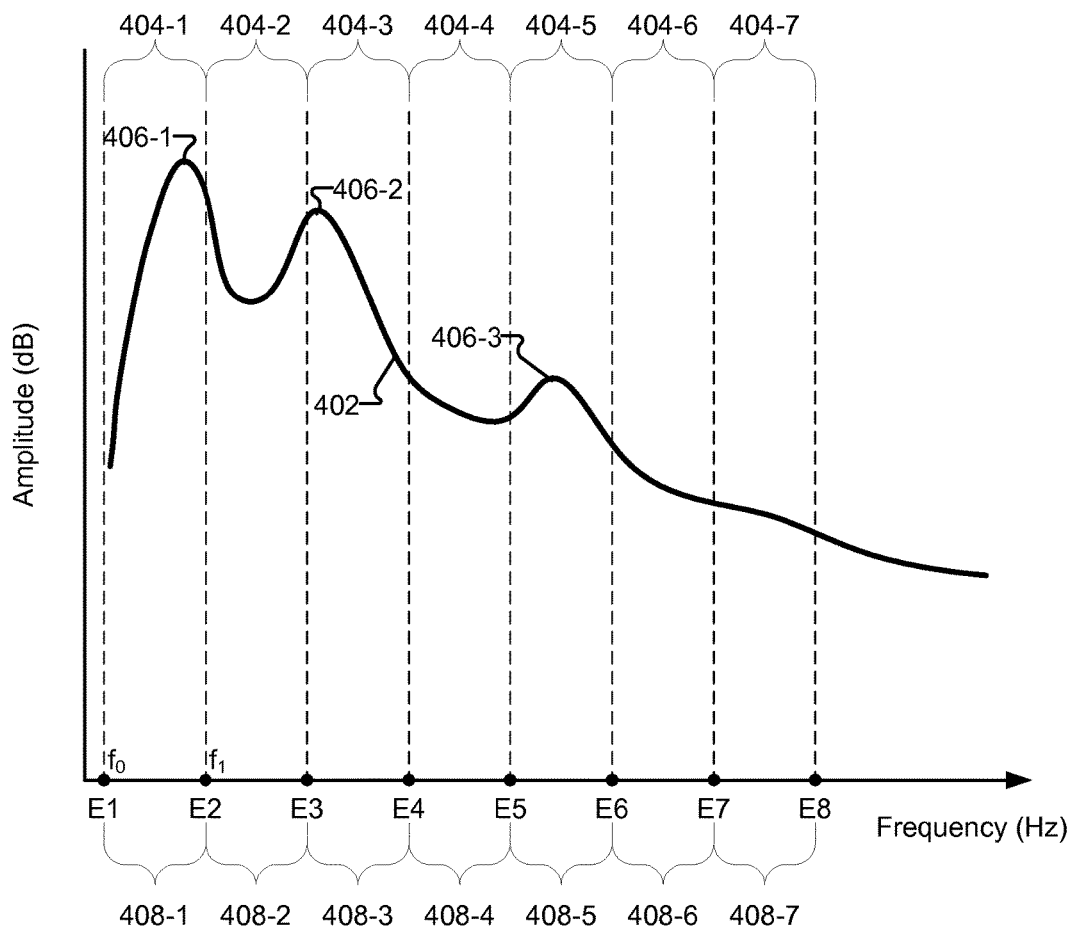
FIG. 4 shows an exemplary frequency domain representation of an audio signal that may be presented to a cochlear implant patient according to principles described herein.

To illustrate, FIG. 4 shows an exemplary frequency domain representation of an audio signal 402 that may be presented to a cochlear implant patient. As illustrated by the dashed vertical lines, processing facility 302 has divided the audio signal 402 into a plurality of analysis channels 404-1 through 404-7 (collectively "analysis channels 404"). Each analysis channel 404 corresponds to a particular frequency band. For example, analysis channel 404-1 corresponds to a frequency band defined by frequencies $f_0$ and $f_1$. While seven analysis channels 404 are shown in FIG. 4, it will be recognized that processing facility 302 may divide the audio signal 402 into any number of analysis channels as may serve a particular application.

Each analysis channel 404 may contain a frequency domain signal representative of a distinct frequency portion of audio signal 402. For example, the portion of audio signal 402 that is included in the frequency band defined by frequencies $f_0$ and $f_1$ may be referred to as the frequency domain signal (or acoustic content) contained within analysis channel 404-1.

As illustrated in FIG. 4, various spectral peaks 406 (e.g., spectral peaks 406-1 through 406-3) may be located within one or more of analysis channels 404. These spectral peaks 406 may represent the distinguishing or meaningful frequency components of audio signal 402. For example, if audio signal 402 includes speech, spectral peaks 406 may be representative of formants included in the speech. As used herein, a formant represents a resonance of the human vocal tract and is associated with the utterance of a vowel sound.

Each analysis channel 404 may correspond to a stimulation channel 408 (e.g., stimulation channels 408-1 through 408-7). Each stimulation channel 408 may be defined by one or more electrodes (e.g., one or more of electrodes E1 through E8). In the particular example of FIG. 4, each stimulation channel 408 is defined by two electrodes. For example, stimulation channel 408-1, which corresponds to analysis channel 404-1, is defined by electrodes E1 and E2. Likewise, stimulation channel 408-2, which corresponds to analysis channel 404-2, is defined by electrodes E2 and E3. While FIG. 4 shows a one-to-one mapping of analysis channels 404 to stimulation channels 408, it will be recognized that multiple analysis channels may be mapped to a single stimulation channel as may serve a particular implementation.

Each electrode may be located at a position within the cochlea (or any other structure within the patient) that corresponds to a stimulation site associated with a particular frequency. For example, electrode E1 is located at a position that corresponds to a stimulation site associated with frequency $f_0$. Hence, stimulation of electrode E1 by itself may result in the patient perceiving frequency $f_0$. As will be described below, to represent acoustic content having a frequency that corresponds to a stimulation site located in between stimulation sites associated with two electrodes, current steering between the two electrodes may be used. It will be recognized, however, that the correspondence between the electrode location and the associated spectral region may not be exact, but could depend on, among other factors, electrode placement and unique anatomical features of an individual patient.

As mentioned, each stimulation channel 408 may be defined by one or more electrodes. However, any number of electrodes may correspond to the stimulation channel 408. For example, electrodes E2 and E3 define stimulation channel 408-2 shown in FIG. 4. However, electrodes E1 through E4 may correspond to stimulation channel 408-2 in that main current may be applied to one or more of electrodes E1 through E4 to represent an audio signal (e.g., a spectral peak) included in analysis channel 404-2 and in that compensating current may be applied to one or more of electrodes E1 through E4 to either focus (i.e., narrow) or defocus (i.e., widen) an excitation field produced by the main current.

Figure 5:
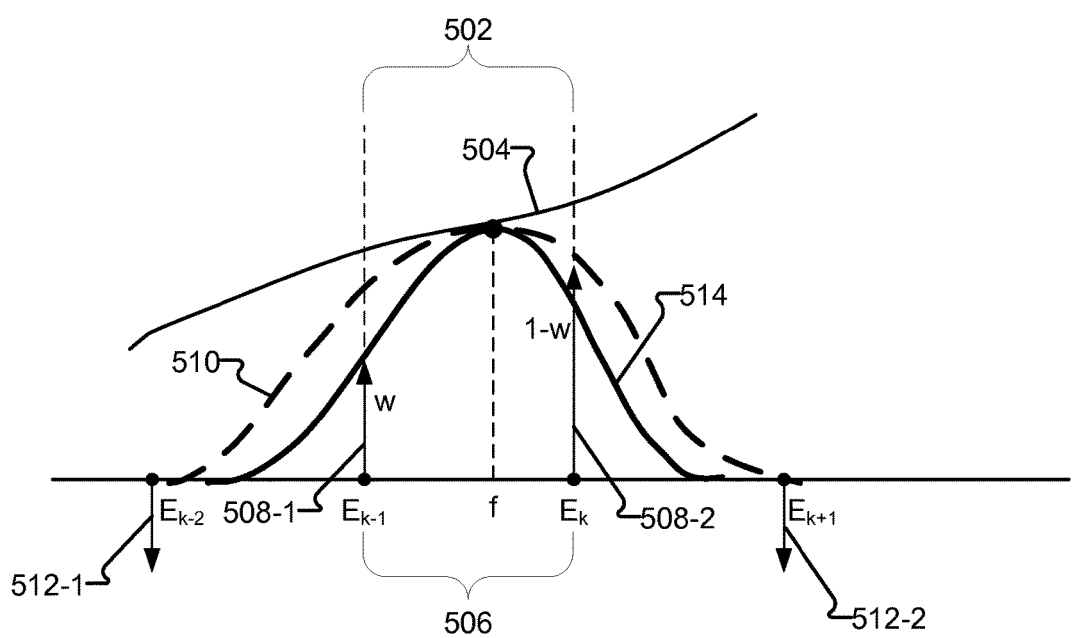
FIGS. 5-7 illustrate various focusing and defocusing stimulation strategies according to principles described herein.

To illustrate, FIG. 5 shows an exemplary analysis channel 502 that contains a frequency domain signal 504. In the example of FIG. 5, analysis channel 502 corresponds to a stimulation channel 506 corresponding to four electrodes—electrodes $E_{k-2}$, $E_{k-1}$, $E_k$, and $E_{k+1}$. In this configuration, current steering between electrodes $E_{k-1}$ and $E_k$ may be used to represent frequency domain signal 504.

For example, FIG. 5 shows that main current 508-1 having a weighted amplitude of w and main current 508-2 having a weighted amplitude of 1−w are concurrently applied to electrodes $E_{k-1}$ and $E_k$, respectively. This results in a peak envelope located at frequency f. In the absence of focusing (i.e., if no compensating current is applied to one or more electrodes surrounding electrodes $E_{k-1}$ and $E_k$), the excitation field associated with the peak envelope is relatively broad, as represented by envelope 510.

However, in accordance with a stimulation strategy that includes focusing (referred to herein as a "focusing stimulation strategy"), compensating current 512-1 and 512-2 (collectively "compensating current 512") opposite in polarity compared to that of main current 508-1 and 508-2 (collectively "main current 508") may be applied to electrodes $E_{k-2}$ and $E_{k+1}$ concurrently with the application of main current 508-1 and 508-2 to electrodes $E_{k-1}$ and $E_k$. As shown, electrodes $E_{k-2}$ and $E_{k+1}$ surround electrodes $E_{k-1}$ and $E_k$. Compensating current 512 serves to focus the excitation field associated with the peak envelope, as represented by envelope 514. It will be recognized that compensating current may be applied by way of any number of compensating electrodes.

As shown in FIG. 5, the polarity of the main current 508 has been set to be positive and the polarity of the compensating current 512 has been set to be negative. The negative polarity of the compensating current 512 serves to focus or narrow the excitation field created by the main current 508. In contrast, if the polarity of the compensating current 512 is set to have the same polarity as the main current 508, the compensating current 512 may defocus or widen the excitation field generated by the main current 508.

Figure 6:
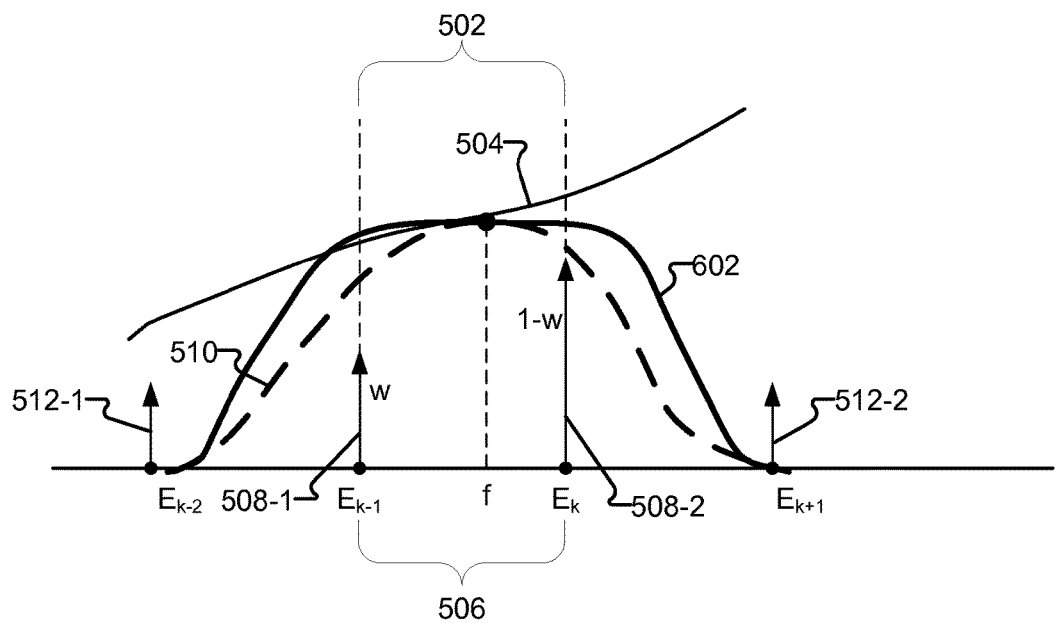

To illustrate, FIG. 6 is similar to FIG. 5, except that the compensating current 512 is of the same polarity as the main current 508 (i.e., the compensating current 512 has a positive polarity). As shown, this results in an excitation field (represented by envelope 602) that is defocused or widened compared to the excitation field represented by envelope 510.

As will be described below, the systems and methods described herein facilitate dynamic selection of which electrodes are to be designated as main electrodes and which electrodes are to be designated as compensating electrodes, dynamic determination of an amount (i.e., amplitude) of main current to be applied to each of the designated main electrodes and amount (i.e., amplitude) of compensating current to be applied to each of the compensating electrodes, and a polarity of the main current and the compensating current. In this manner, the systems and methods described herein may allow a cochlear implant system to more accurately emulate the functioning of a normal ear by attempting to maintain a relatively constant excitation field width for any given stimulation channel, regardless of where the stimulation site is within the channel.

To this end, processing facility 302 may identify a stimulation site within a cochlea of a patient that is to be stimulated in order to represent acoustic content presented to the patient. As described above, the acoustic content may be a frequency domain signal representative of a distinct frequency portion of an audio signal presented to the patient. The stimulation site may be included within a plurality of stimulation sites associated with a stimulation channel corresponding to a plurality of electrodes. For example, referring to FIG. 4, the identified stimulation site may be included within a plurality of stimulation sites associated with stimulation channel 408-2. To illustrate, the stimulation site may correspond to a first edge of stimulation channel 408-2 (i.e., be located at a position directly stimulated by electrode E2), a middle of stimulation channel 408-2 (i.e., be located at a position in between locations directly stimulated by electrodes E2 and E3), or a second edge of stimulation channel 408-2 (i.e., be located at a position directly stimulated by electrode E3). It will be recognized that any number of stimulation sites may be associated with a stimulation channel.

Processing facility 302 may identify a stimulation site within a cochlea of a patient that is to be stimulated in order to represent acoustic content presented to the patient in any suitable manner. For example, processing facility 302 may determine a frequency of a spectral peak included in an analysis channel that corresponds to the frequency channel. Processing facility 302 may then identify a stimulation site that corresponds to the identified frequency. For example, in order to represent the acoustic content included in analysis channel 404-1, processing facility 302 may determine a frequency of spectral peak 406-1 and identify a stimulation site that corresponds to the frequency of spectral peak 406-1. Alternatively, a stimulation site may be determined after psychophysical masking principles are applied to determine the shape of the spectrum as it would be presented in the auditory system of a normally-hearing individual.

Stimulation management facility 304 may be configured to manage (e.g., control) stimulation provided by cochlear implant 108. For example, as mentioned, processing facility 302 may identify a stimulation site that is to be stimulated in order to represent an audio signal presented to the patient and that is associated with a stimulation channel that corresponds to a plurality of electrodes. In response, stimulation management facility 304 may determine a target excitation field width associated with the stimulation channel and dynamically set, based on the identified stimulation site, an amplitude and a polarity of current to be applied to each electrode included in the plurality of electrodes in order to represent the acoustic content so that an excitation field created by the current has a width that roughly matches the target excitation field width. Stimulation management facility 304 may then direct cochlear implant 108 to stimulate the identified stimulation site by applying the current to the plurality of electrodes.

Stimulation management facility 304 may determine a target excitation field width associated with the stimulation channel in any suitable manner. For example, the target excitation field width may be set during a fitting procedure in which the cochlear implant system is fitted to the patient. Data representative of the set target excitation field width may be stored within storage facility 306 or within a storage medium residing within cochlear implant 108. Stimulation management facility 304 may accordingly determine the target excitation field width associated with the stimulation channel by accessing the stored data.

Additionally or alternatively, stimulation management facility 304 may determine the target excitation field width associated with the stimulation channel by receiving user input representative of the target excitation field width. The user input may be provided by the patient, a clinician, or any other user. In this manner, the user may manually adjust the target excitation field width as desired in order to create a desired noise level associated with the stimulation channel.

Additionally or alternatively, stimulation management facility 304 may determine the target excitation field width associated with the stimulation channel based on an excitation field width associated with one or more other stimulation events performed with respect to the stimulation channel. For example, stimulation management facility 304 may direct cochlear implant 108 to apply current to a plurality of electrodes corresponding to a stimulation channel in order to represent acoustic content presented to the patient. Stimulation management facility 304 may identify (e.g., measure) an excitation field width of an excitation field created by the current. The identified excitation field width may be designated as the target excitation field width. Stimulation management facility 304 may then receive additional acoustic content presented to the patient subsequent to the acoustic content being presented to the patient. Stimulation management facility 304 may dynamically set an amplitude and a polarity of additional current to be applied to each electrode included in the plurality of electrodes in order to represent the additional acoustic content so that an excitation field created by the additional current has a width that roughly matches the identified excitation field width (which, in this case, is the target excitation field width).

Stimulation management facility 304 may dynamically set the amplitude and the polarity of the current that is to be applied to each electrode included in the plurality of electrodes in order to represent acoustic content in any suitable manner. For example, the dynamic setting may be performed in accordance with a focusing stimulation strategy.

To illustrate, it has been observed that unfocused stimulation (i.e., application of main current in the absence of compensating current) of a stimulation site located towards the center of a stimulation channel results in an excitation field that is relatively wider than an excitation field created by unfocused stimulation of a stimulation site located towards or at the edge of the stimulation channel. Hence, in some examples, in order to achieve a relatively constant excitation field width regardless of the location of the stimulation site within the stimulation channel, relatively more focusing may be used when stimulating stimulation sites located towards the center of the stimulation channel than when stimulating stimulation sites located towards the edge of the stimulation channel. In other words, the degree of focusing used may be a function of stimulation site location, and may increase the closer the stimulation site is to the center of the stimulation channel.

To illustrate, four electrodes may correspond to the stimulation channel associated with the identified stimulation site—a first electrode, a second electrode, a third electrode, and a fourth electrode sequentially disposed within the cochlea. The first electrode is the most apically disposed of the four electrodes and the fourth electrode is the most basally disposed of the four electrodes. The identified stimulation site may be in between a stimulation site associated with the second electrode and a stimulation site associated with the third electrode. In this example, stimulation management facility 304 may perform the dynamic setting by using the identified stimulation site and the determined target excitation field width to 1) designate the second and third electrodes as being main electrodes to which main current having a positive polarity is applied to represent the acoustic content, 2) designate the first and fourth electrodes as being compensating electrodes to which compensating current having a negative polarity is applied to focus the excitation field created by the main current, 3) determine a first weighted amount of the main current to be applied to the second electrode in accordance with a current steering strategy, 4) determine a second weighted amount of the main current to be applied to the third electrode in accordance with the current steering strategy, 5) determine a first weighted amount of the compensating current to be applied to the first electrode, and 6) determine a second weighted amount of the compensating current to be applied to the fourth electrode. By appropriately setting the weighted amounts of main current and compensating current, the excitation field may be centered at the identified stimulation site and have a width roughly equal to the target excitation field width.

To illustrate, reference is again made to FIG. 5. In this example, the identified stimulation site corresponds to the frequency f and the target excitation field width is the width of the excitation field represented by envelope 514. To stimulate the identified stimulation site with current that results in an excitation field that has the target excitation field width, stimulation management facility 304 may designate electrodes $E_{k-1}$ and $E_k$ as main electrodes and electrodes $E_{k-2}$ and $E_{k+1}$ as compensating electrodes, set the polarity of the main current 508 to be positive and the polarity of the compensating current 512 to be negative, and set the weighted amounts of current to be applied to each electrode to an appropriate amount.

Once the weighted amounts of main current and compensating current have been set, as well as the polarities of the main current and the compensating current, stimulation management facility 304 may direct cochlear implant 108 to stimulate the identified stimulation site by concurrently applying the main current and the compensating current to the first, second, third, and fourth electrodes. In this particular example, cochlear implant 108 may concurrently apply the first weighted amount of the main current to the second electrode, the second weighted amount of the main current to the third electrode, the first weighted amount of the compensating current to the first electrode, and the second weighted amount of the compensating current to the fourth electrode. Stimulation management facility 304 may direct cochlear implant 108 to apply these weighted amounts of current to the electrodes in any suitable manner. For example, stimulation management facility 304 may transmit four words to cochlear implant 108. Each word may include any suitable number of bits that may be used by cochlear implant 108 to generate and apply particular amounts of current to each electrode. For example, the first word may direct cochlear implant 108 to apply the first weighted amount of the main current to the second electrode. The second word may direct cochlear implant 108 to apply the second weighted amount of the main current to the third electrode. The third word may direct cochlear implant 108 to apply the first weighted amount of the compensating current to the first electrode. The fourth word may direct cochlear implant 108 to apply the second weighted amount of the compensating current to the fourth electrode.

Stimulation management facility 304 may additionally or alternatively perform the dynamic setting in accordance with a defocusing stimulation strategy. For example, continuing with the example in which four electrodes correspond to the stimulation channel, the identified stimulation site may be associated with the second electrode (i.e., located at the left edge of the stimulation channel). In this case, stimulation management facility 304 may perform the dynamic setting by 1) designating the second electrode as being a lone main electrode to which main current having a positive polarity is applied to represent the acoustic content, the main current creating the excitation field, 2) designating the first and third electrodes as being compensating electrodes to which compensating current having a positive polarity is applied to defocus the excitation field, 3) determining the main current to be applied to the second electrode, 4) determining a first weighted amount of the compensating current to be applied to the first electrode, and 5) determining a second weighted amount of the compensating current to be applied to the third electrode. By appropriately setting the amplitudes of the main current and compensating current, the excitation field may be centered at the identified stimulation site and have a width roughly equal to the target excitation field width.

Continuing with this example, stimulation management facility 304 may direct cochlear implant 108 to stimulate the identified stimulation site by concurrently applying the main current to the second electrode, the first weighted amount of the compensating current to the first electrode, and the second weighted amount of the compensating current to the third electrode. The current is applied to these three electrodes while cochlear implant 108 abstains from applying current to the fourth electrode.

Figure 7:
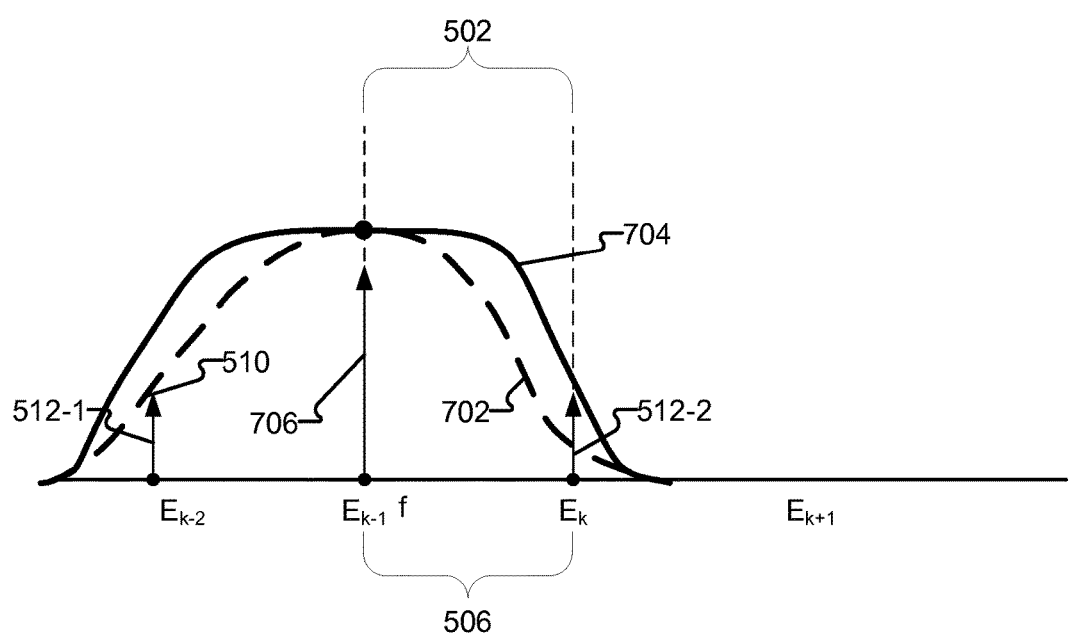

To illustrate, reference is again made to FIG. 7. FIG. 7 shows the same stimulation channel 502 shown in FIGS. 5-6. However, in FIG. 7, the identified stimulation site is associated with electrode $E_{k-1}$ (i.e., the identified stimulation site is located at the left edge of stimulation channel 502). In this particular example, envelope 702 represents the excitation field that would be generated in the absence of compensating current and envelope 704 represents the target excitation field associated with stimulation channel 502.

To stimulate the identified stimulation site with current that results in an excitation field that has the target excitation field width, stimulation management facility 304 may designate electrodes $E_{k-1}$ as the lone main electrode and electrodes $E_{k-2}$ and $E_k$ as compensating electrodes. In this instance, no current is to be applied to electrode $E_{k+1}$. To broaden the excitation field, stimulation management facility 304 may set the polarity of both the main current 706 and the compensating current 512-1 and 512-2 to be positive. The amplitude of current to be applied to each electrode may be set to an appropriate amount to result in stimulation of the identified stimulation site.

It will be recognized that various other stimulation strategies may be used in accordance with the systems and methods described herein. For example, any of the stimulation strategies described in co-pending PCT Application No. PCT/US13/72494, entitled "Focusing Systems and Methods for Use in a Cochlear Implant System," filed the same day as the present application and incorporated herein by reference in its entirety, may be used in accordance with the systems and methods described herein to dynamically control a width of an excitation field created by stimulation of a stimulation site.

In some examples, the dynamic setting by stimulation management facility 304 of the amplitude and the polarity of the different currents that are to be applied to a group of electrodes in order to represent acoustic content may be further based on a loudness level of the acoustic content. It has been observed that relatively loud sounds result in relatively wide excitation fields and that relatively quiet sounds result in relatively narrow excitation fields in normally functioning ears. Hence, to emulate this, stimulation management facility 304 may take the loudness level of the acoustic content into account when performing the dynamic setting.

For example, stimulation management facility 304 may determine that the loudness level of the acoustic content is above a predetermined threshold (the predetermined threshold may be determined in any suitable manner). In response, the dynamic setting may be performed in accordance with a defocusing stimulation strategy. Likewise, if the loudness level of the acoustic content is equal to or below the predetermined threshold, the dynamic setting may be performed in accordance with a focusing stimulation strategy. Examples of this are provided in more detail in U.S. Pat. No. 7,769,467, the contents of which are hereby incorporated by reference in their entirety. It will be recognized that the degree of focusing and/or defocusing used may vary in any suitable manner as a function of loudness level.

Additionally or alternatively, the dynamic setting by stimulation management facility 304 of the amplitude and the polarity of the different currents that are to be applied to a group of electrodes in order to represent acoustic content may be further based on a frequency of the acoustic content relative to the other frequencies in an overall frequency spectrum. For example, it may be desirable to provide relatively more focusing at relatively high frequencies and relatively less focusing at relatively low frequencies. Hence, in some examples, if stimulation management facility 304 determines that the frequency of the acoustic content is above a predetermined threshold, stimulation management facility 304 may perform the dynamic setting in accordance with a focusing stimulation strategy. Likewise, if the frequency of the acoustic content is equal to or below the predetermined threshold, the dynamic setting may be performed in accordance with a defocusing stimulation strategy.

Stimulation management facility 304 may use any computational heuristic to dynamically set the amplitude and the polarity of the current to be applied to each electrode. For example, stimulation management facility 304 may dynamically set the amplitude and the polarity of the current to be applied to each electrode in accordance with a vector math heuristic.

Figure 8:
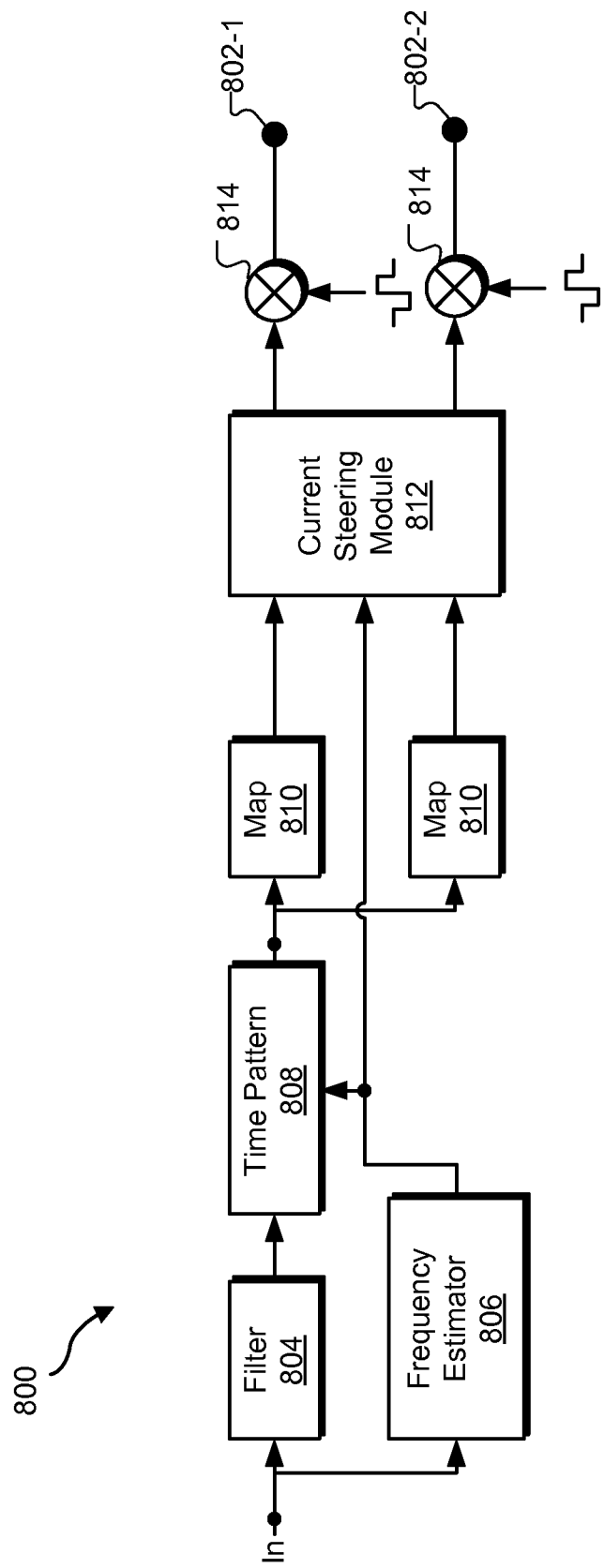
FIG. 8 illustrates an exemplary implementation of current steering according to principles described herein.

FIG. 8 illustrates an exemplary implementation 800 of current steering that may be used in connection with any of the stimulation strategies described herein. The components and functions illustrated in FIG. 8 may be implemented by any of the systems, facilities, and/or modules described herein. For example, one or more components of sound processor 104 may be configured to perform any of the functions described in connection with FIG. 8.

As shown in FIG. 8, current steering may be applied to two or more electrodes 802 (e.g., electrodes 802-1 and 802-2). Two electrodes 802 are shown in FIG. 8 for illustrative purposes only. It will be recognized that current steering may alternatively be applied to three or more electrodes as may serve a particular application. Electrodes 802-1 and 802-2 may be adjacent one to another (i.e., no other electrode 802 is physically disposed in between them on a lead). Alternatively, electrodes 802-1 and 802-2 may be non-adjacent (i.e., one or more electrodes 802 are physically disposed in between them on a lead).

As shown in FIG. 8, an input signal may be filtered by at least one filter 804 configured to generate a frequency domain signal representative of a distinct frequency portion of the audio signal. The input signal is also input into a frequency estimator 806 configured to estimate the peak frequency thereof. A time pattern block 808 is configured to build the temporal structure of a pulse train representing the signal output by the at least one filter 804. Mapping modules 810 are configured to map the amplitude of the signal output by the time pattern block 808 to corresponding current levels in accordance with a suitable mapping function.

The output of each mapping module 810 is input into a current steering module 812. The current steering module 812 is also configured to receive the output of the frequency estimator 806. In some examples, the current steering module 812 is configured to determine appropriate weighting factors for current to be applied to electrodes 802-1 and 802-2. This determination may be based at least in part on the peak frequency estimate and the output of each of the mapping modules 810. The weighting factors may be applied to the current using multiplication blocks 814. In this manner, stimulation current may be delivered to a stimulation site located in between areas associated with electrodes 802-1 and 802-2.

Figure 9:
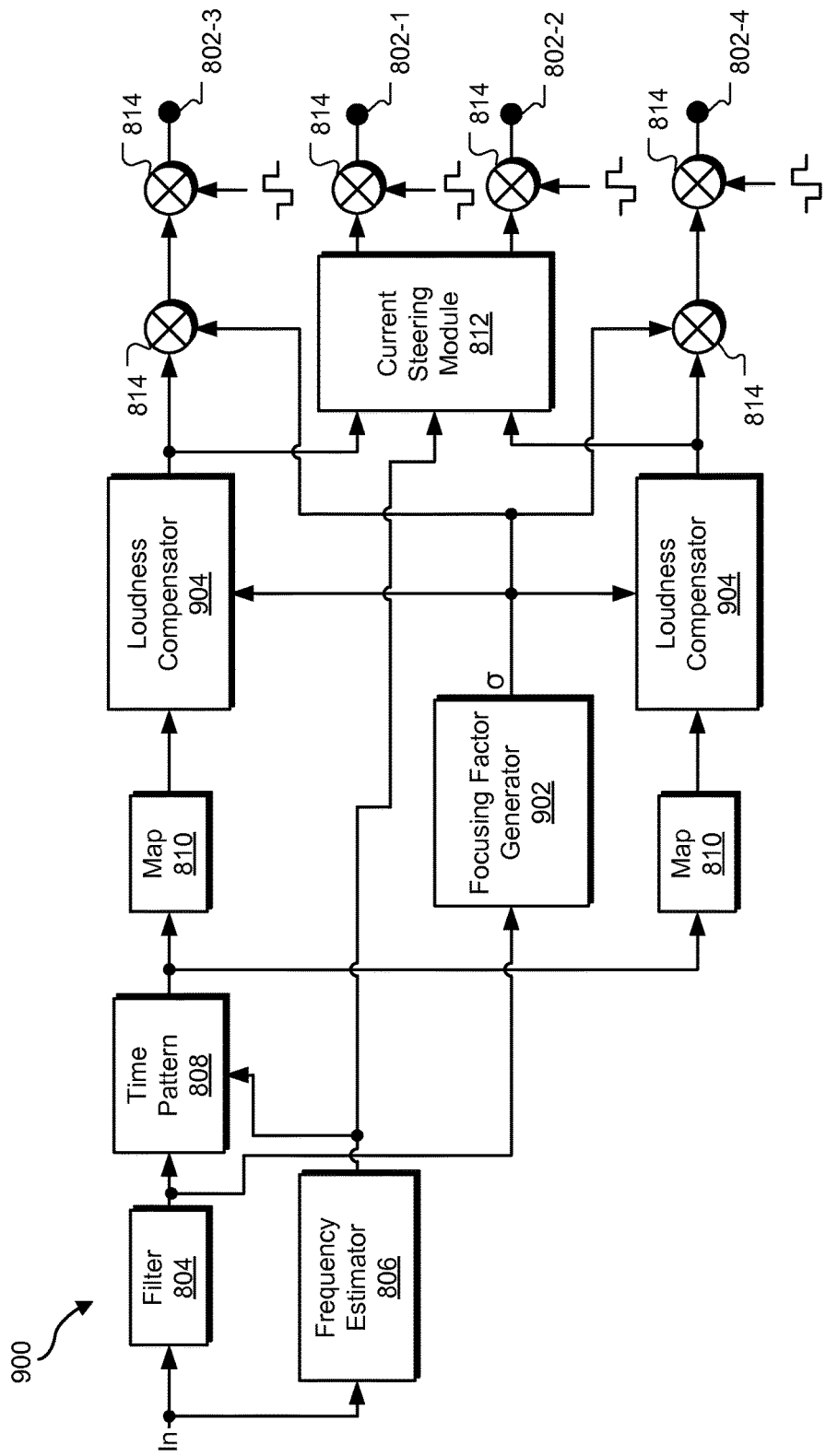
FIG. 9 illustrates another exemplary implementation of current steering that may be used to dynamically focus or defocus one or more excitation fields produced by current steering electrodes according to principles described herein.

The excitation field produced by the current steering electrodes 802-1 and 802-2 may be focused by applying compensating current simultaneously to one or more additional electrodes (referred to herein as compensating electrodes). To illustrate, FIG. 9 illustrates another exemplary implementation 900 of a current steering strategy that may be used to dynamically focus or defocus one or more excitation fields produced by current steering electrodes (e.g., electrodes 802-1 and 802-2). The components and functions illustrated in FIG. 9 may be implemented by any of the systems, facilities, and/or modules described herein. For example, one or more components of sound processor 104 may be configured to perform any of the functions described in connection with FIG. 9.

Implementation 900 includes many of the same components as the implementation described in connection with FIG. 8. In addition, functional block diagram 900 includes a focusing factor generator 902 configured to generate focusing factor σ based on the amplitude of the signal output by filter 804. The focusing factor σ is used to generate scaled versions of the current steering current. This scaled current is delivered via one or more additional electrodes (e.g., electrodes 802-3 and 802-4) to effectively focus or defocus the excitation field produced by electrodes 802-1 and 802-2.

As shown in FIG. 9, loudness compensators 904 may also be included within the implementation 900 of FIG. 9. Loudness compensators 904 are configured to adjust the amplitudes of the currents applied via electrodes 802-1 and 802-2 to compensate for loudness changes that may be caused by current delivered via the compensating electrodes 802-3 and 802-4.

While exemplary implementations 800 and 900 of current steering have been described herein, it will be recognized that other implementations of current steering may be additionally or alternatively used in connection with the systems and methods described herein as may serve a particular implementation.

Figure 10:
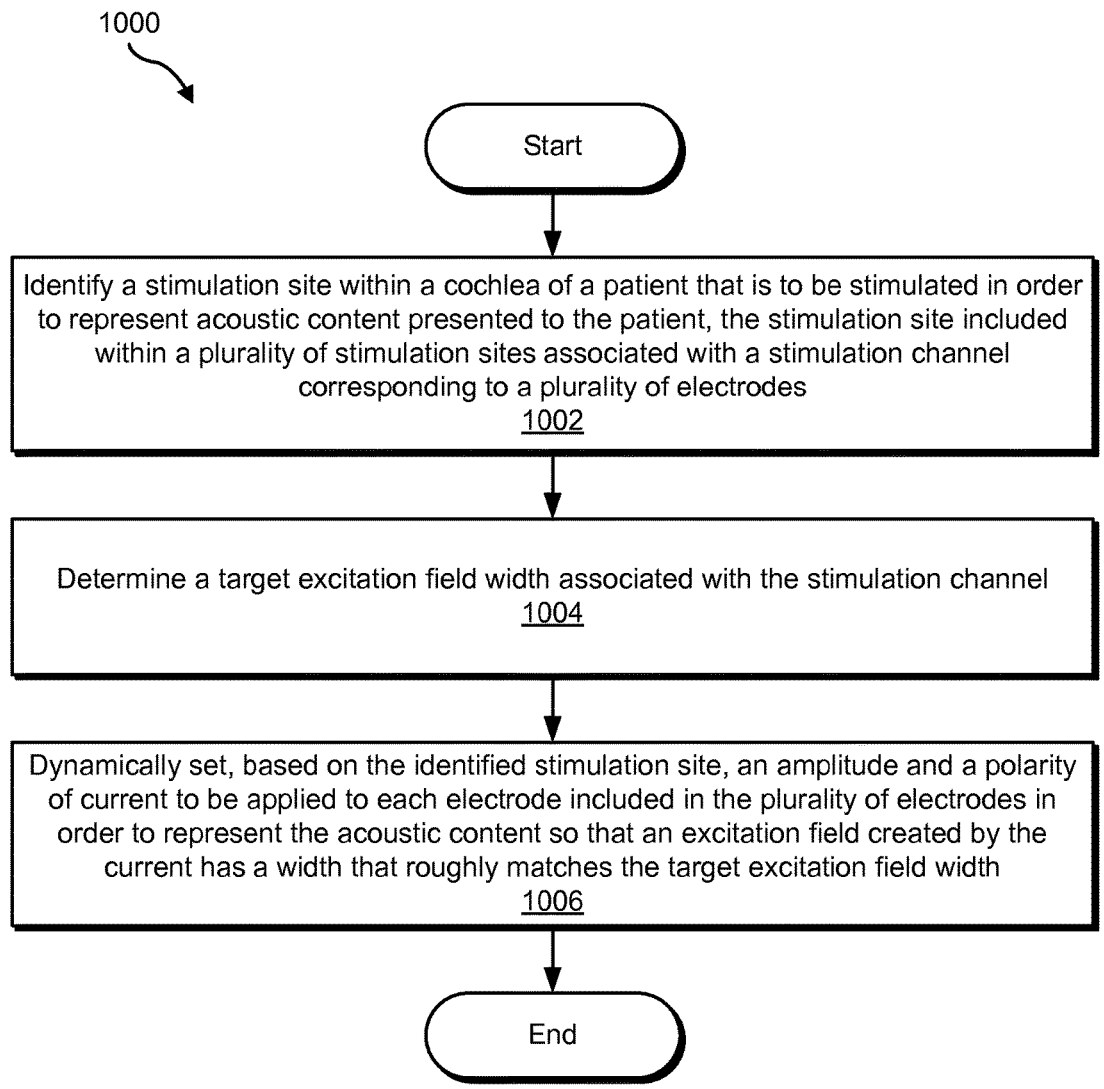
FIG. 10 illustrates an exemplary method according to principles described herein.

FIG. 10 illustrates an exemplary method 1000. While FIG. 10 illustrates exemplary steps according to one embodiment, other embodiments may omit, add to, reorder, and/or modify any of the steps shown in FIG. 10. One or more of the steps shown in FIG. 10 may be performed by sound processor 104 and/or any implementation thereof.

In step 1002, a sound processor identifies a stimulation site within a cochlea of a patient that is to be stimulated in order to represent acoustic content presented to the patient. As described above, the stimulation site is included within a plurality of stimulation sites associated with a stimulation channel corresponding to a plurality of electrodes. Step 1002 may be performed in any of the ways described herein.

In step 1004, the sound processor determines a target excitation field width associated with the stimulation channel. Step 1004 may be performed in any of the ways described herein.

In step 1006, the sound processor dynamically sets, based on the identified stimulation site, an amplitude and a polarity of current to be applied to each electrode included in the plurality of electrodes in order to represent the acoustic content so that an excitation field created by the current has a width that roughly matches the target excitation field width. Step 1006 may be performed in any of the ways described herein.

In the preceding description, various exemplary embodiments have been described with reference to the accompanying drawings. It will, however, be evident that various modifications and changes may be made thereto, and additional embodiments may be implemented, without departing from the scope of the invention as set forth in the claims that follow. For example, certain features of one embodiment described herein may be combined with or substituted for features of another embodiment described herein. The description and drawings are accordingly to be regarded in an illustrative rather than a restrictive sense.

What is claimed is:

1. A system comprising:
   a processing facility that identifies a stimulation site within a cochlea of a patient that is to be stimulated in order to represent acoustic content presented to the patient, the stimulation site included within a plurality of stimulation sites associated with a stimulation channel corresponding to a plurality of electrodes, the plurality of electrodes including one or more main electrodes and two or more compensating electrodes; and
   a stimulation management facility communicatively coupled to the processing facility and that
      determines a target excitation field width associated with the stimulation channel,
      dynamically sets, based on the identified stimulation site, an amplitude and a polarity of main current to be applied to the one or more main electrodes in order to create an excitation field representative of the acoustic content, and
      dynamically sets, based on the identified stimulation site and the target excitation field width, an amplitude and a polarity of compensating current to be applied to each of the two or more compensating electrodes in order to focus or defocus the excitation field created by the main current to have a width that roughly matches the target excitation field width.

2. The system of claim 1, wherein the stimulation management facility directs a cochlear implant associated with the patient to stimulate the identified stimulation site by applying the current to the plurality of electrodes.

3. The system of claim 1, wherein:
   the plurality of electrodes including the one or more main electrodes and the two or more compensating electrodes comprises a first electrode, a second electrode, a third electrode, and a fourth electrode sequentially disposed within the cochlea;
   the identified stimulation site is in between a stimulation site associated with the second electrode and a stimulation site associated with the third electrode; and
   the stimulation management facility performs the dynamic setting by
      designating the second and third electrodes as being the one or more main electrodes and the first and fourth electrodes as being the two or more compensating electrodes,
      determining the polarity of main current to be applied to the one or more main electrodes to be a positive polarity in order to create the excitation field and the polarity of the compensating current to be a negative polarity in order to focus the excitation field,
      determining a first weighted amount of the main current to be applied to the second electrode in accordance with a current steering strategy,
      determining a second weighted amount of the main current to be applied to the third electrode in accordance with the current steering strategy,
      determining a first weighted amount of the compensating current to be applied to the first electrode, and
      determining a second weighted amount of the compensating current to be applied to the fourth electrode.

4. The system of claim 3, wherein the stimulation management facility directs a cochlear implant associated with the patient to stimulate the identified stimulation site by concurrently:
   applying the first weighted amount of the main current to the second electrode;
   applying the second weighted amount of the main current to the third electrode;
   applying the first weighted amount of the compensating current to the first electrode; and
   applying the second weighted amount of the compensating current to the fourth electrode.

5. The system of claim 4, wherein the stimulation management facility performs the directing by transmitting, to the cochlear implant:
   a first word that directs the cochlear implant to apply the first weighted amount of the main current to the second electrode;
   a second word that directs the cochlear implant to apply the second weighted amount of the main current to the third electrode;
   a third word that directs the cochlear implant to apply the first weighted amount of the compensating current to the first electrode; and
   a fourth word that directs the cochlear implant to apply the second weighted amount of the compensating current to the fourth electrode.

6. The system of claim 1, wherein:
   the plurality of electrodes including the one or more main electrodes and the two or more compensating electrodes comprises a first electrode, a second electrode, a third electrode, and a fourth electrode sequentially disposed within the cochlea;
   the identified stimulation site is associated with the second electrode; and
   the stimulation management facility performs the dynamic setting by designating only the second electrode as being the one or more main electrodes and the first and third electrodes as being the two or more compensating electrodes, determining the polarity of main current to be applied to the one or more main electrodes to be a positive polarity in order to create the excitation field and the polarity of the compensating current to be a positive polarity in order to defocus the excitation field, determining the main current to be applied to the second electrode, determining a first weighted amount of the compensating current to be applied to the first electrode, and determining a second weighted amount of the compensating current to be applied to the third electrode.

7. The system of claim 6, wherein the stimulation management facility directs a cochlear implant associated with the patient to stimulate the identified stimulation site by concurrently:

applying the main current to the second electrode;

applying the first weighted amount of the compensating current to the first electrode;

applying the second weighted amount of the compensating current to the third electrode; and abstaining from applying current to the fourth electrode.

8. The system of claim 1, wherein the dynamic setting is performed in accordance with a focusing stimulation strategy.

9. The system of claim 1, wherein the dynamic setting is performed in accordance with a defocusing stimulation strategy.

10. The system of claim 1, wherein the dynamic setting is further based on a loudness level of the acoustic content.

11. The system of claim 10, wherein the stimulation management facility:

determines that the loudness level of the acoustic content is above a predetermined threshold; and performs, in response to the determination that the loudness level is above the predetermined threshold, the dynamic setting in accordance with a defocusing stimulation strategy.

12. The system of claim 10, wherein the stimulation management facility:

determines that the loudness level of the acoustic content is equal to or below a predetermined threshold; and performs, in response to the determination that the loudness level is equal to or below the predetermined threshold, the dynamic setting in accordance with a focusing stimulation strategy.

13. The system of claim 1, wherein the dynamic setting is further based on a frequency of the acoustic content.

14. The system of claim 13, wherein the stimulation management facility:

determines that the frequency of the acoustic content is above a predetermined threshold; and performs, in response to the determination that the frequency is above the predetermined threshold, the dynamic setting in accordance with a focusing stimulation strategy.

15. The system of claim 13, wherein the stimulation management facility:

determines that the frequency of the acoustic content is equal to or below a predetermined threshold; and performs, in response to the determination that the frequency is equal to or below the predetermined threshold, the dynamic setting in accordance with a defocusing stimulation strategy.

16. The system of claim 1, wherein the stimulation management facility determines the target excitation field width associated with the stimulation channel by:

detecting a width of an excitation field created by current applied to the electrodes in order to represent additional acoustic content presented to the patient prior to the acoustic content being presented to the patient; and designating the detected width as the target excitation field width associated with the stimulation channel.

17. The system of claim 1, wherein the stimulation management facility determines the target excitation field width associated with the stimulation channel by receiving user input representative of the target excitation field width associated with the stimulation channel.

18. A sound processor included in a cochlear implant system associated with a patient, the sound processor comprising:

at least one processor that directs a cochlear implant included in the cochlear implant system to apply current to a plurality of electrodes corresponding to a stimulation channel in order to represent acoustic content presented to the patient, the plurality of electrodes including one or more main electrodes and two or more compensating electrodes, identifies an excitation field width of an excitation field created by the current, receives additional acoustic content presented to the patient subsequent to the acoustic content being presented to the patient, dynamically sets an amplitude and a polarity of a main current to be applied to the one or more main electrodes in order to create an excitation field representative of the additional acoustic content, and dynamically sets, based on the identified excitation field width, an amplitude and a polarity of a compensating current to be applied to each of the two or more compensating electrodes in order to focus or defocus the excitation field created by the main current to have a width that roughly matches the identified excitation field width.

19. The sound processor of claim 18, wherein the at least one processor directs the cochlear implant to apply the additional current to the plurality of electrodes in order to represent the additional acoustic content.

20. A method comprising:

identifying, by a sound processor, a stimulation site within a cochlea of a patient that is to be stimulated in order to represent acoustic content presented to the patient, the stimulation site included within a plurality of stimulation sites associated with a stimulation channel corresponding to a plurality of electrodes, the plurality of electrodes including one or more main electrodes and two or more compensating electrodes;

determining, by the sound processor, a target excitation field width associated with the stimulation channel;

dynamically setting, by the sound processor based on the identified stimulation site, an amplitude and a polarity of main current to be applied to the one or more main electrodes in order to create an excitation field representative of the acoustic content; and dynamically setting, by the sound processor based on the identified stimulation site and the target excitation field width, an amplitude and a polarity of compensating current to be applied to each of the two or more compensating electrodes in order to focus or defocus the excitation field created by the main current to have a width that roughly matches the target excitation field width.

* * * * *